(12) United States Patent
Conrad

(10) Patent No.: US 8,252,213 B2
(45) Date of Patent: Aug. 28, 2012

(54) DENTURE FLASK MOULD PRESS AND METHOD OF USE

(76) Inventor: Paul Kingsley Newton Conrad, St. Thomas (CA)

( * ) Notice: Subject to any disclaimer, the term of this patent is extended or adjusted under 35 U.S.C. 154(b) by 773 days.

(21) Appl. No.: 12/033,980

(22) Filed: Feb. 20, 2008

(65) Prior Publication Data

US 2008/0197532 A1    Aug. 21, 2008

Related U.S. Application Data

(60) Provisional application No. 60/890,732, filed on Feb. 20, 2007.

(51) Int. Cl.
*B28B 7/04* (2006.01)
(52) U.S. Cl. ............ 264/39; 264/16; 264/17; 264/18; 264/19; 264/20; 249/54; 433/147; 433/3; 433/153; 433/155
(58) Field of Classification Search ............ 264/663, 264/307, 16–20, 39, 138–139, 317; 433/147, 433/3, 153, 155; 249/54
See application file for complete search history.

(56) References Cited

U.S. PATENT DOCUMENTS 2,102,266 A * 12/1937 Handler ............... 425/178

* cited by examiner

*Primary Examiner* — Jeffrey Wollschlager
*Assistant Examiner* — Stella Yi

(57) ABSTRACT

In preparing dentures, hardened mould material surrounds the denture. This mould material is adhered inside a denture flask with a housing having two separably matable portions. To remove the hardened mould material from the flask, the flask is mounted in a mould press having a shaft, with one of the portions is restrained against movement along an axis of travel of the shaft. A portion of the mould material at an end of the restrained flask portion is available for contact with the shaft along the axis of travel. A capped end of the shaft is forcefully advanced against the adhered mould material therein, thereby breaking the adhesion. After this is done, the denture flask is dismounted from the mould press and the hardened mould material is removed from the first flask portion. If necessary, the process is repeated with the other housing portion.

3 Claims, 5 Drawing Sheets

DENTURE FLASK MOULD PRESS AND METHOD OF USE

CROSS-REFERENCE TO RELATED APPLICATIONS

This application is a non-provisional of U.S. Ser. No. 60/890,732, filed 20 Feb. 2007, which is incorporated by reference as if fully recited herein.

TECHNICAL FIELD

The invention relates to a mould press used to extract denture mould material from a denture flask.

BACKGROUND OF THE ART

It is known in the art to use a multi-piece device, generally referred to as a denture flask, as the structure in which dentures, either original or duplicates, are cast.

In preparing a denture, the mould material is contained in a sectional, box-like case referred to in the art as a denture flask. The mould material surrounds a model of the denture being formed. The model can be either an existing denture or a positive impression of the denture to be formed. One example of a prior art flask is taught in U.S. Pat. No. 5,607,628 to Palazzolo.

Obtaining a strong, dense and aesthetically superior denture requires that the mould material be compressed at least prior to curing, and, preferably, during curing, to remove porosity and to closely correspond the mould material to the denture model. While a press may be used in this process, especially for expressing excess mould material from the flask, the press is not used for removing the hardened mould material in which the cured denture is embedded.

The process of curing the denture and the pressure imposed during the process can render the removal of the mould material (with the embedded denture) difficult. In a known method, the closure plate at one end of the flask is removed and the mould material is withdrawn from the flask cavity by careful manipulation with tools such as a hammer, chisels and the like.

It is therefore an object of the present invention to provide a mould press that can facilitate the removal of the mould material from the cavity after the curing process, thereby minimizing the losses of product occasioned by breakage or damage during the removal process.

SUMMARY OF THE INVENTION

This and other objects of the invention are achieved by a method for removing hardened mould material from an adhered condition in a denture flask. The denture flask comprises a housing with at least two portions that are separably mated to each along a joinder line parallel to the ends of the denture flask. The housing is substantially filled with the hardened mould material, in which a denture is being formed. One step is to mount the denture flask in a mould press, with the joinder line positioned radially with respect to an axis of travel of a shaft of the mould press. The first flask portion is restrained against movement along the axis of travel, with at least a portion of the mould material at an end of the first flask portion available for contact with the shaft along the axis of travel. In another step, a capped end of the shaft is advanced towards the denture flask and the adhered mould material therein, thereby breaking the adhesion of the mould material to the first flask portion. After this is done, the denture flask is dismounted from the mould press and the hardened mould material is removed from the first flask portion.

If necessary, the method also comprises the steps of removing the hardened mould material from the second flask portion. To do this, the second flask portion is mounted in the mould press, with the second flask portion restrained against movement along the axis of travel and with at least a portion of the mould material at an end of the second flask portion available for contact along the axis of travel. The capped end of the shaft is advanced towards the second flask portion, breaking the adhesion of the mould material to the second flask portion. The second flask portion is then dismounted from the mould press and the hardened mould material is removed from the second flask portion.

In many of the methods, the step of advancing the capped end of the shaft is accomplished by the rotation of a threaded portion of the shaft in a frame of the mould press.

In many of the methods, the hardened mould material is available for contact by removing an end cap of the denture flask portion being acted upon. In other variations of the method, the hardened mould material is available for contact through an aperture in the end of the flask portion being acted upon.

In many of the methods, the flask portion being acted upon restrained from movement along the axis of travel by engaging a restraining member on an exterior of the flask portion with a corresponding restraining member on the mould press. In a particular version of the method, the restraining member on the flask portion is a groove formed in the surface and the restraining member on the mould press is a flange.

BRIEF DESCRIPTION OF THE DRAWINGS

The Invention will be better understood when reference is made to the accompanying drawings, where identical parts are identified with identical part numbers and wherein.

DETAILED DESCRIPTION OF THE PREFERRED EMBODIMENT

Figure 1:
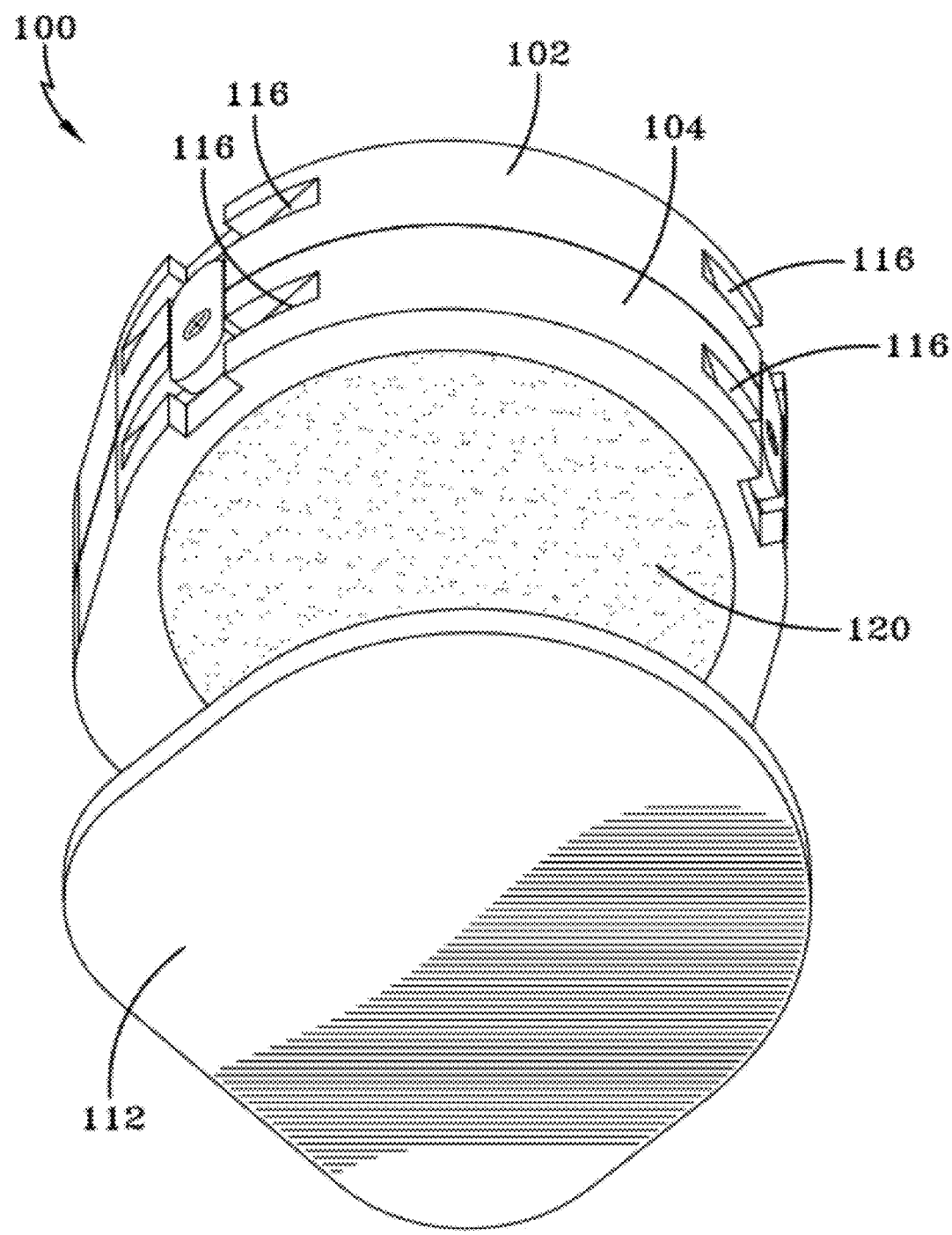
FIG. 1 is a perspective view of a dental flask with the closure on one side removed to reveal the denture related mould material within.
Figure 2:
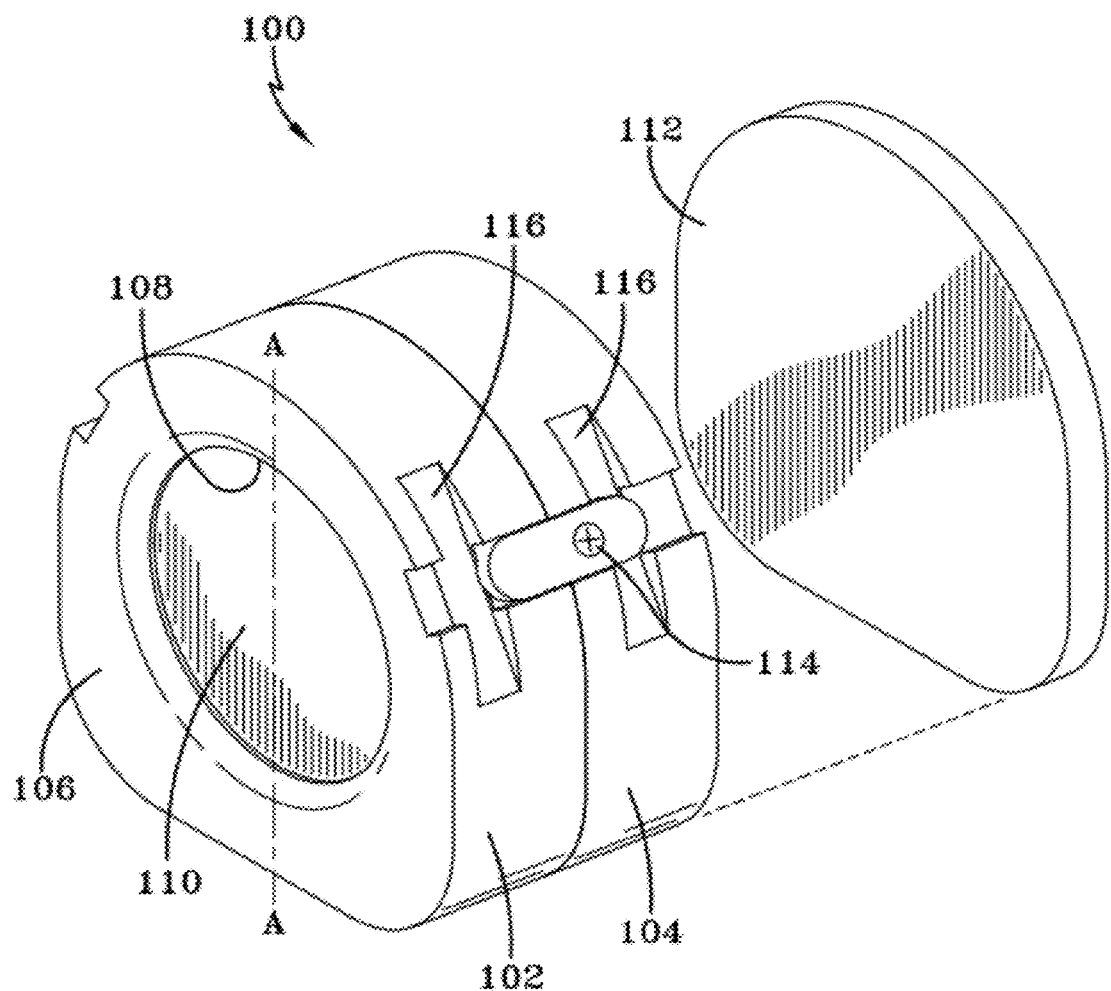
FIG. 2 is a perspective view of the denture flask shown in FIG. 1.
Figure 4:
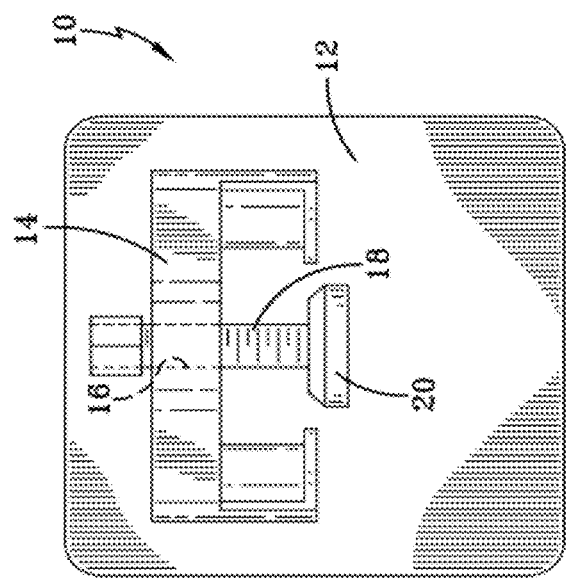
FIG. 4 is a top plan view of the FIG. 3 mould press.
Figure 6:
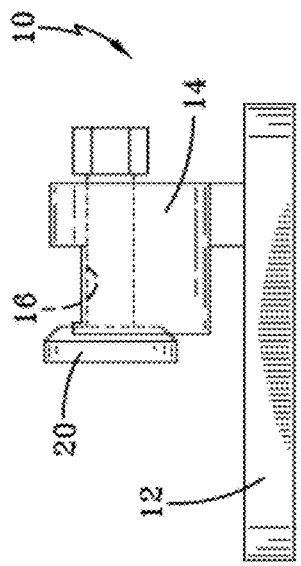
FIG. 6 is a side elevation view of the FIG. 3 mould press.
Figure 3:
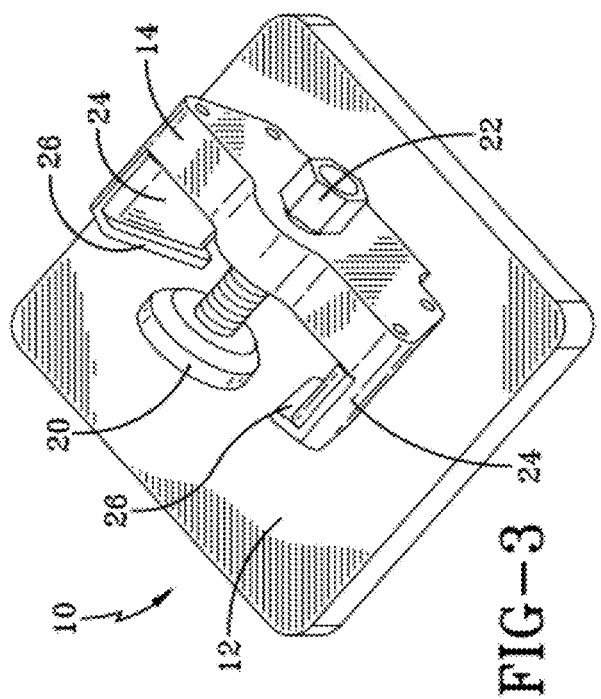
FIG. 3 is a perspective view of a first embodiment mould press.
Figure 5:
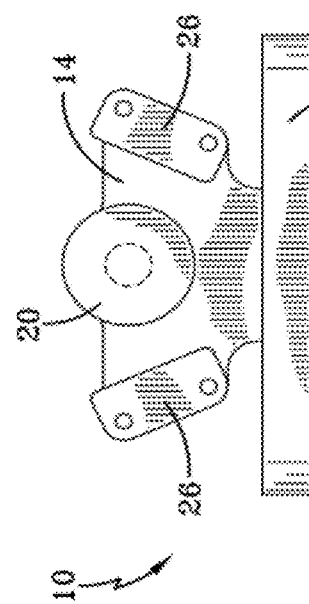
FIG. 5 is a front elevation view of the FIG. 3 mould press.

Referring first to FIGS. 1 and 2, it is known to use a denture flask 100 to prepare denture-related mould material 120 as is known in the art. The particular dental flask 100 depicted in FIGS. 1 and 2 is an embodiment manufactured by Buffalo Dental Company. A flask 100 of this type will commonly comprise a metal material, particularly brass. The flask 100 comprises a housing defining a cavity within. The housing is formed from several parts, including a first portion 102 and a second portion 104. Of these portions, first portion 102 is provided an open first end that mates with a corresponding open first end of the second portion 104. The first portion 102 is provided on its second end with a partially-closed end face 106 having a centrally placed aperture 108. For example, aperture 108 is centered on an axis of symmetry, shown as line A-A of the flask 100. In use, a knock-out plate 110 is placed into the first portion 102 prior to the addition of any mould material, effectively covering the aperture 108. The second portion 104 is open at each end, the previously-mentioned first end facing a mating open end of the first portion. Instead of having a partially open second end, second portion 104 is closed by means of a closure plate 112. The first and second housing portions 102, 104 may be held in their mating positions by a variety of known fastening means, such as the fasteners 114 shown in FIG. 2.

Another feature shown in FIGS. 1 and 2 is a plurality of grooves 116 that are provided on the respective portions 102, 104. These grooves 116 run in a circumferential direction relative to a longitudinal axis of the flask 100. These grooves 116 may be used, for example, for mechanically grasping the portions 102, 104 in pressing together or separating the portions.

Keeping in mind the fact that the flask is used for preparing a denture that will fit in the upper or lower (maxillary or mandibular) arch of the wearer, it is a practical consideration to minimize the amount of excess mould material. Since the respective arches are generally "U"-shaped, narrowing in width as one moves in the anterior direction, a preferred profile for a denture flask will be a trapezoidal shape.

Attention is now directed to FIGS. 3 through 6, which show an embodiment of the mould press 10 in perspective, top plan, front elevation and side elevation views, respectively. In many embodiments, the mould press 10 comprises a base 12 upon which the operative press components may be mounted. In some embodiments, the frame 14 of the press 10 may be formed integrally with, or attached directly to, the base 12. In either case, frame 14 is provided with a threaded shaft-receiving bore 16, into which a correspondingly threaded shaft 18 is received. In a preferred embodiment, the shaft 18 passes normally through a central portion of the frame 14. The shaft 18 is provided at a first end with a flask-engaging cap 20 and at a second end with a head 22, adapted for rotating the shaft 18. In the specific embodiment illustrated, the head 22 is enlarged and has a hexagonal profile, adapted for use with a wrench. In other embodiments, such as FIG. 7 described below, the head 222 could be adapted for receiving an Allen wrench or the like. In a yet further embodiment, the head 22 could have a transverse bore for receiving a bar that would constitute a handle for manual turning of the shaft 18. In any of these cases, the head 22 would be a fixed attachment to the shaft 18 that provides a means for rotating the shaft in either direction, advancing or withdrawing the cap 20 relative to the frame 14. For the initial installation of the shaft 18 in the bore 16, the cap 20 will generally be removably affixed to the shaft. In some situations, the cap 20 will be threadingly affixed, while in other instances, the cap 20 will be affixed with a swivel linkage.

Symmetrically positioned relative to the shaft 18, and on the same side of the frame 14 as the cap 20, is a pair of arms 24, each of which has a flange 26 that extends towards a longitudinal axis of the shaft 18. The arms 24 and flanges 26 are angled with respect to each other for capturing the grooves 116 formed on either side of the flask 100 shown and described above. In fact, the most preferred embodiments would have the mould press 10 particularly adapted for use with a specific flask 100. When the flask 100 has a trapezoidal profile, as suggested above, it would be appropriate to have the arms 24 spaced apart and angled relative to each other appropriately for receiving the flask.

Figure 7:
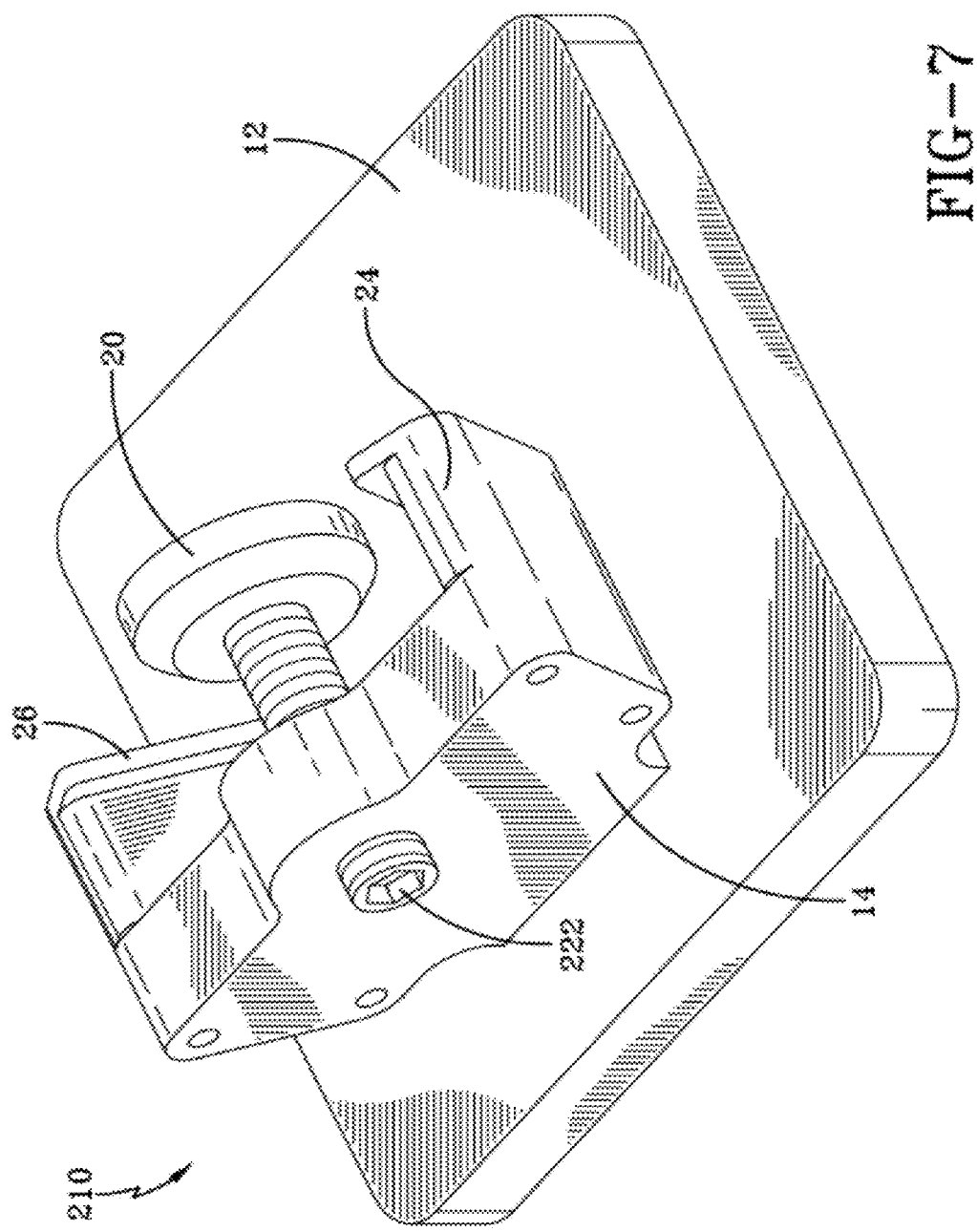
FIG. 7 is a perspective view of a second embodiment mould press.

FIG. 7 shows a perspective view of an second embodiment of the mould press 210 similar to that of FIGS. 3-6, but in which the enlarged hexagonal head is replaced with a head 222 adapted for receiving an Allen wrench.

Figure 8:
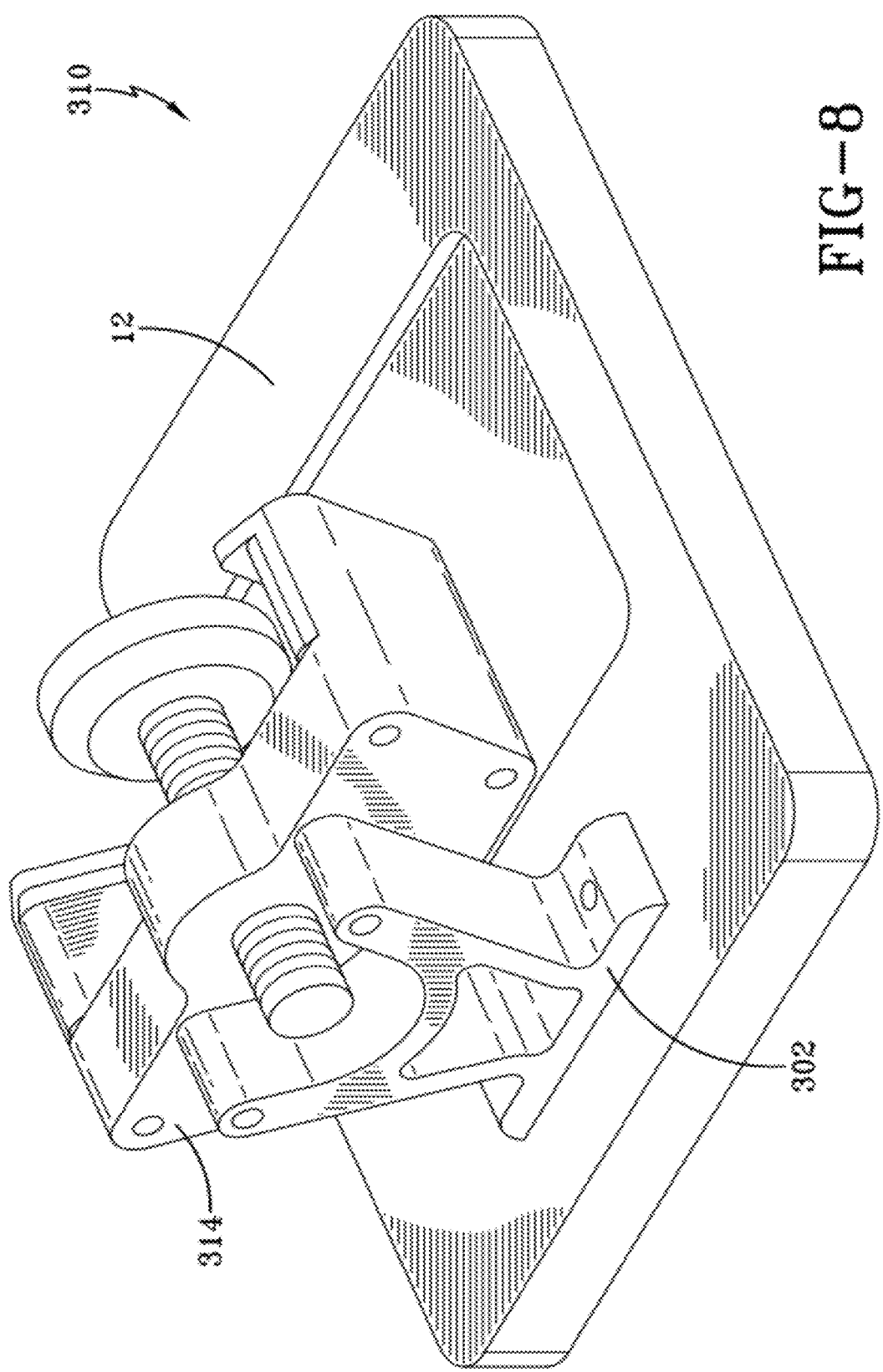
FIG. 8 is a perspective view of a third embodiment mould press.

FIG. 8 shows a perspective view of a third embodiment of the mould press 310 similar to that of FIGS. 3 through 6. In this embodiment, the frame 314 is not directly attached to the base 12, but is instead attached to the base by means of a support member 302.

To use the mould press 10 for removing a mass of hardened mould material from inside a denture flask such as the flask 100 taught herein, the closure plate 112 is removed from the flask 100, exposing the open end of second portion 104. The flask 100 is then mounted in the mould press 10. In doing this, the flask 100 is oriented so that the partially-closed end face 106 points toward the flask-engaging cap 20 of the mould press 10, and the open end of the flask second portion 104 points away from the mould press. The flanges 26 of the mould press 10 engage the grooves 116 on the first portion 102 of the flask 100, and the flask rests generally upon the arms 24, securing the flask within the press.

In this position, flask-engaging cap 20 is axially aligned with the aperture 108, so the cap 20 is advanced towards (and contacts) the knock-out plate 110. Applying pressure to the hardened mass of material inside the flask 100 as it is advanced against the knock out plate 110, the shaft 18 loosens the adhesion of the hardened material to the interior wall of the flask, and, particularly, the adhesion to the interior wall of the first portion 102. When the cap 20 has advanced into the flask about as far as the joinder line between the first and second portions 102, 104, the shaft 18 is turned in the opposite direction, so that the cap 20 disengages the flask 100, allowing the flask to be removed from the mould press 10. At this point, the first portion 102 is conveniently disengaged from the second portion 104, and the hardened mass of mould material will likely remain lodged in the second portion 104, although in some instances, it is possible that the mould material can be manually removed from the second portion without further use of the mould press 10. In such an instance, the removal of the mould material from the flask 100 is completed.

If, as in most cases, the mould material remains lodged, the second portion 104 of the flask 100 is inserted into the press, with the flanges 26 of the mould press 10 engaging the grooves 116 on the second portion 104, the second portion resting generally upon the arms 24, and securing the second portion in the press. The mould material that has been forced out of the flask faces axially away from the shaft 18 and its cap 20. In many instances, the knock out plate 110 will still be adhered to the hardened mould material. The cap 20 is advanced by rotation of the shaft 18 into contact with the hardened mould material (either directly, if the knock out plate is not intact, or indirectly, if it is intact). After advancing the cap 20 the second time into a flask portion, the hardened mould material is removed from the second portion 104.

The mould press 10 as taught above can be suitably adapted to work with most flasks on the same described principle.

What is claimed is:

1. A method for removing hardened mould material from an adhered condition in a denture flask, the denture flask comprising a housing having a first flask portion and a second flask portion separably mated to each other along a joinder line that is parallel to the ends of the denture flask, each flask portion having a groove, the housing substantially filled with the hardened mould material, the method comprising the steps of:

mounting the denture flask in a mould press having a flange, the joinder line positioned radially with respect to an axis of travel of a shaft of the mould press with at least a portion of the mould material at an end of the first flask portion available for contact with the shaft along the axis of travel, the availability being through an open end of the first flask portion or an aperture in the end of the first flask portion and restraining the first flask portion against movement along the axis of travel by engaging the flange on the mould press with the groove on the first flask portion;

advancing a capped end of the shaft towards the denture flask and the adhered mould material therein, breaking the adhesion of the mould material to the first flask portion;

dismounting the denture flask from the mould press and removing the first flask portion from the hardened mould material;

mounting the second flask portion in the mould press, with at least a portion of the mould material at an end of the second flask portion available for contact along the axis of travel and restraining the second flask portion against movement along the axis of travel by engaging the flange on the mould press with the groove on the second flask portion;

advancing the capped end towards the second flask portion, breaking the adhesion of the mould material to the second flask portion; and dismounting the second flask portion from the mould press and removing the second flask portion from the hardened mould material.

2. The method of claim 1, wherein:
the advancing step is accomplished by threadingly rotating the shaft.

3. The method of claim 1, wherein:
in the mounting step, the mould material is available for contact by removing an end cap of the denture flask.

* * * * *